United States Patent

Kahsnitz et al.

Patent Number: 5,461,144
Date of Patent: * Oct. 24, 1995

[54] PROCESS FOR THE PREPARATION OF ALKYL POLYGLYCOSIDES

[75] Inventors: John Kahsnitz; Stefan Schmidt, both of Haltern; Alfred Oberholz, Marl, all of Germany

[73] Assignee: Huels Aktiengesellschaft, Marl, Germany

[*] Notice: The portion of the term of this patent subsequent to Jul. 15, 2010 has been disclaimed.

[21] Appl. No.: 150,796

[22] Filed: Nov. 12, 1993

Related U.S. Application Data

[63] Continuation of Ser. No. 863,710, Apr. 3, 1992, abandoned, which is a continuation of Ser. No. 624,647, Dec. 10, 1990, abandoned.

[30] Foreign Application Priority Data

May 22, 1991 [DE] Germany ............ 41 16 665.5

[51] Int. Cl.$^6$ .................. C07H 1/00; C07H 3/00; C07H 15/04

[52] U.S. Cl. .................. 536/18.6; 536/124

[58] Field of Search ................ 536/18.5, 18.6, 536/124

[56] References Cited

U.S. PATENT DOCUMENTS

| | | | |
|---|---|---|---|
| 2,606,186 | 8/1952 | Dean et al. | 536/18.6 |
| 3,450,690 | 6/1969 | Gibbons et al. | 536/18.5 |
| 4,329,449 | 5/1982 | Roth et al. | 536/120 |
| 4,847,368 | 7/1989 | Lueders et al. | 536/18.6 |
| 4,866,165 | 9/1989 | Lüders | 536/18.6 |
| 4,898,934 | 2/1990 | Lueders et al. | 536/18.6 |
| 4,950,743 | 8/1990 | McCurry, Jr. et al. | 536/18.6 |
| 5,079,350 | 1/1992 | Fujita et al. | 536/18.6 |
| 5,227,480 | 7/1993 | Oberholz et al. | 536/18.5 |

*Primary Examiner*—Michael G. Wityshyn
*Assistant Examiner*—Everett White
*Attorney, Agent, or Firm*—Oblon, Spivak, McClelland, Maier & Neustadt

[57] ABSTRACT

$C_{8-18}$ alkylpolyglycosides are prepared by reacting a $C_{1-6}$ alkyl glycoside with a $C_{8-18}$ alcohol in a reaction column.

11 Claims, 1 Drawing Sheet

PROCESS FOR THE PREPARATION OF ALKYL POLYGLYCOSIDES

This application is a continuation of Ser. No. 07/863,710, filed on Apr. 3, 1992, now abandoned, which is a continuation of Ser. No. 07/624,647, filed Dec. 10, 1990, now abandoned.

BACKGROUND OF THE INVENTION

FIELD OF THE INVENTION

The present invention relates to an improved process for the preparation of alkyl polyglycosides by reaction of alkyl glycosides containing alkyl groups of 1 to 6 C atoms with alcohols having 8 to 18 C atoms.

DESCRIPTION OF THE BACKGROUND

Alkyl polyglycosides containing $C_8$- to $C_{18}$-alkyl radicals can entirely or in part be prepared from renewable raw materials. Because of their interesting surfactant properties in combination with very good biodegradability, these alkyl polyglycosides are increasingly gaining importance. These materials have to meet high aesthetic requirements for household and cosmetic applications. Accordingly, interest is directed towards processes by which alkyl polyglycosides can be prepared with reduced thermal stress as transparent, aqueous solutions of attractive color.

According to the disclosure of U.S. Pat. No. 4,950,743, glucose monohydrate is reacted directly with a long-chain alcohol. Before the reaction can be initiated by adding the catalyst, the water of hydration must first be largely removed by applying a vacuum. Likewise, in a two-step procedure, first glucose monohydrate is dehydrated almost quantitatively using butanol under a vacuum, before butyl glucoside is prepared after adding the catalyst. The product is then reacted in a stirred reactor with long-chain alcohols. After the reaction is complete, the mixture is neutralized and the color is improved, preferably by reduction with $NaBH_4$.

In the direct reaction with long-chain alcohols, this process requires a dehydration step and subsequently high reaction times. In addition, phase separation problems occur. In the two-step procedure, another 4.5 hours are required for the second step. The space-time yields are low in this case.

EP 0,377,831 describes a method in which an acid solution of butyl glucoside in butanol is metered during transglycosylation, into a long-chain alcohol in a stirred reactor which has been pre-heated to 100° to 125° C. and which may contain an acid catalyst. Here the product is exposed to fairly long thermal stress. In addition, the space-time yield of this process is not yet fully satisfactory. A need therefore continues to exist for a method of transglycosylation which results in improved space-time yield of alkyl polyglycoside product.

SUMMARY OF THE INVENTION

Accordingly, one object of the present invention is to improve the space-time yield of the transglycosylation reaction and to simultaneously reduce the thermal stress of product and starting compounds.

Briefly, this object and other objects of the present invention as hereinafter will become more readily apparent can be attained by preparing $C_{8-18}$ alkyl polyglycosides by reacting a $C_{1-8}$ alkyl glycoside with a $C_{8-18}$ alcohol in a reaction column.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein the FIGURE shows a column reactor as employed in the process embodiment of Example 1.

DETAILED DESCRIPTION OF THE PREFERRED EMBODIMENTS

Figure 1:
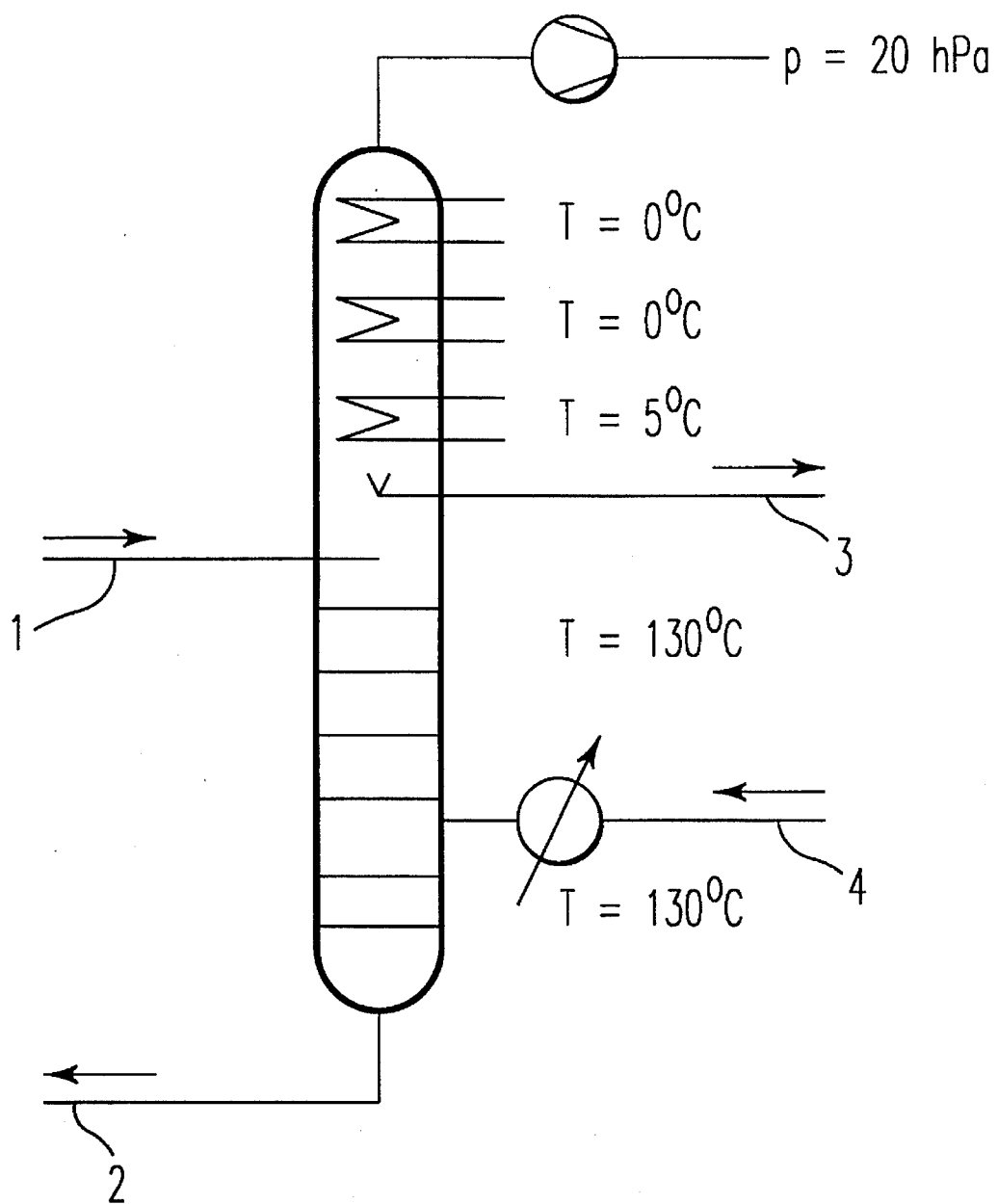

The improvements of the present invention have been achieved by conducting the transglycosylation reaction in a reaction column. Suitable examples of reaction columns include bubble-cap, sieve-plate, tunnel-cap or packed columns. The columns preferably have 2 to 15 actual plates, and columns having 2 to 10 actual plates are very particularly preferred. The columns can be operated in a co- or counter-current or, in a preferred embodiment, in a modified counter-current manner. In the co-current procedure, the reaction components are introduced into the upper portion of the column.

In the context of this invention, the upper portion of the column is understood to mean the effective upper quarter of the column. This includes the column head and, where appropriate, some of the upper plates. Fitted columns or column parts for condensing distillates are not taken into account.

The reacting components employed are the alkyl glycoside containing an alkyl group of 1 to 6 C atoms, the alcohol having 8 to 18 C atoms and the catalyst. The alkyl glycoside used here can be prepared, for example, in a stirred reactor, a reaction tube, a reaction column or even in a combination of reactors. In a preferred embodiment, at least 10% of the alcohol having 8 to 18 C atoms is introduced together with the remaining components used into the upper portion of the column. However, up to 90% of this long-chain alcohol is introduced into the lower portion of the column. The lower portion of the column is understood to mean the effective lower half of the column.

In a particularly preferred embodiment, 20 to 80% of the long-chain alcohol is introduced into the lower portion of the column in vapor form. In this case, transglycosylation also takes place under counter-current conditions. A modified counter-current procedure is given if excess long-chain alcohol is not discharged at the top, but at the bottom of the column.

The sugar content of the alkyl glycosides used can be derived, for example, from glucose, mannose, galactose or gulose. Examples of alkyl groups include methyl, ethyl, butyl, pentyl and hexyl groups. The alkyl glycosides used can, to a small extent, also be oligomerized. Thus, products having average degrees of oligomerization of 1 to 2 are also considered alkyl glycosides in the context of this invention.

The alkyl glycosides are preferably used together with an alcohol having 1 to 6 C atoms. Examples of suitable alcohols includes methanol, ethanol, butanol, pentanol and hexanol. In particular, up to 5 parts by weight of alcohol having 1 to 6 C atoms, relative to the alkyl glycoside, are additionally used.

In a highly preferred embodiment, butyl glucoside is used for the transglycosylation together with n-butanol. Suitable examples of long-chain alcohols include octanol, nonanol, decanol, dodecanol, tetradecanol and hexadecanol.

The alkyl glycoside and long-chain alcohol of 8 to 18 C atoms are preferably used in a molar ratio of 1:2 to 1:15. These molar ratios very particularly preferably range from 1:4 to 1:10.

Suitable catalysts for the reaction include, in particular, mineral acids such as sulfuric or phosphoric acid and strong organic acids such as benzenesulfonic acid, cumenesulfonic acid and p-toluenesulfonic acid and also acid ion exchangers. Catalysts which are preferably used include organic acids, because of their relatively low corrosive action.

The transglycosylation reaction is in most cases carried out at temperatures ranging from 100° to 180° C. Of these, temperatures from 120° to 140° C. are preferred. Although the reaction can also be carried out at atmospheric pressure or at superatmospheric pressure, it is preferred to use reduced pressure. Reduced pressures of 10 to 500 hPa are very particularly preferred.

The alkyl polyglycosides containing alkyl groups of 8 to 18 C atoms and prepared by the present process in general have average degrees of polymerization ranging from 1.1 to 5. The average degree of polymerization preferably ranges form 1.2 to 3.

In the process according to the invention, the average residence time of the reaction mixture is reduced to a few minutes, for example to 5 to 15 minutes. At the same time, high conversions are obtained. The space-time yield is therefore significantly improved compared with transglycosylation in a stirred reactor.

Alkyl polyglycosides can be prepared continuously by the process according to the invention with simple equipment. Moreover, the products are exposed to little thermal stress in the present process. For this reason, alkyl polyglycosides of improved color can be obtained by this process.

When the modified counter-current procedure is employed, the transglycosylation can, in general, be carried out according to FIG. 1 as follows: Alkyl glycoside, short-chain alcohol, catalyst and a portion of the long-chain alcohol are introduced into the reactor via line 1. Another portion of the long-chain alcohol is introduced into the column as superheated vapor via line 4. In addition, it is also possible to feed inert gas into the still part of the column via this line or via a separate line. The short-chain alcohol introduced and the short-chain alcohol formed during transglycosylation are discharged via line 3. Excess long-chain alcohol and alkyl polyglycoside are cooled and discharged via line 2.

The transglycosylation plant can comprise a column or several columns. Moreover, it can comprise pre- and after-reactors, although the main reaction is carried out in the columns. Because of the pre-reactors, the columns can also be operated with mixtures of substances which have already been reacted to some extent.

After transglycosylation, the reaction mixture is in general neutralized. This neutralization can be carried out by known methods using basic substances, for example using aqueous sodium hydroxide solution.

The distillation of the fatty alcohol which follows can be carried out, for example, in a falling-film or thin-film evaporator. The alcohol which has been distilled off can be recycled and again used for the synthesis. Small amounts of solvent, such as glycols or glycol ethers, can be added to the alkyl polyglycosides formed here.

The alkyl polyglycosides are then bleached. If ozone is used, this bleaching can also be carried out in a bubble column. The products can also be treated with activated carbon, or complexing agents can be added to them.

Having now generally described this invention, a further understanding can be obtained by reference to certain specific examples which are provided herein for purposes of illustration only and are not intended to be limiting unless otherwise specified.

EXAMPLE 1

In a bubble-cap column as shown in FIG. 1 (6 plates, static hold-up=200 ml/plate, D=80 mm, h=100 M/plate), 1.93 mol/h of butyl glucoside, 10.21 mol/h of butanol, 12.70 mol/h of n-dodecanol and 0.060 mol/h of p-toluenesulfonic acid are placed on the first plate (line 1). No further streams are fed into the column. The column is operated at a column head pressure of 20 hPa (absolute pressure) and the temperatures given in FIG. 1. At the column head (line 3) butanol is formed, and in the cold still spot of the column (line 2) fatty alcohol alkyl polyglucoside is formed.

The fatty alcohol alkyl polyglycoside is brought to a pH of 8 to 9 with 5% strength methanolic potassium hydroxide solution. The fatty alcohol is then distilled off in a rotary evaporator. A 50 g amount of the solid obtained is dissolved in 50 ml of water. The pH is brought to 7 by adding 2 N sulfuric acid. 5.3 ml of a 30% strength $H_2O_2$ solution are then added. The mixture is stirred at 80° C. for one hour. 0.2 ml of water glass (sodium silicate solution) is then added, after which the pH is again brought to 7 within 2 N sodium hydroxide solution. After adding 0.2 g of sodium bicarbonate, stirring is continued for another 30 minutes. The iodine color number (ICN) of the solution is determined by comparison with an iodine color scale according to DIN 6162.

| Butyl glucoside conversion: | >68% |
|---|---|
| Average residence time: | 10 min. |
| ICN: | 7–10 |

EXAMPLE 2

In the bubble-cap column of Example 1, 1.96 mol/h of butyl glucoside, 10.18 mol/h of butanol, 6.34 mol/h of n-dodecanol and 0.060 mol/h of p-toluenesulfonic acid are placed on the first plate (line 1). In addition, 6.44 mol/h of n-dodecanol are fed into the column at the 5th plate (line 4) as superheated vapor. The column is operated at a column head pressure of 20 hPa (absolute pressure) and the temperatures given in FIG. 1.

At the column head (line 3) butanol is formed and in the cold still pot of the column (line 2) fatty alcohol alkyl polyglucoside is formed. The work-up procedure is as described in Example 1.

| Butyl glucoside conversion: | >96% |
|---|---|
| Average residence time: | 10 min. |
| ICN: | 7–10 |

EXAMPLE 3

In the bubble-cap column of Example 1, 1.92 mol/h of butyl glucoside, 11.42 mol/h of butanol, 6.77 mol/h of n-dodecanol and 0.060 mol/h of p-toluenesulfonic acid are placed on the first plate (line 1). 6.43 mol/h of n-dodecanol are fed into the column at the 5th plate (line 4) as superheated vapor. Except for the preheating temperature for the fatty alcohol stream (stream 4), which is increased from 130 to 160° C., the temperatures given in FIG. 1 are maintained. The column is operated at a column head pressure of 18 hPa (absolute pressure). At the column head butanol is formed and in the cold still pot of the column fatty alcohol alkyl polyglucoside is formed. The work-up is as described in Example 1.

| Butyl glucoside conversion: | 99.2% |
|---|---|
| Average residence time: | 10 min. |
| ICN: | 7–10 |

Comparative Example A 2.05 l/h of a 35% strength solution of butyl glucoside in butanol, which additionally contains 0.65% of p-toluenesulfonic acid, and 2.5 l/h of fatty alcohol consisting of a mixture of 70% of n-dodecanol and 30% of a n-tetradecanol are introduced into a two-step cascade of stirred reactors comprising two 2.5 l stirred reactors. The stirred reactors are heated to the boiling temperature in vacuo, so that butanol is removed by distillation continuously. The liquid reaction product of the second reactor is an approximately 25% strength solution of alkyl polyglucoside in fatty alcohol.

| Butyl glucoside conversion: | >99% |
|---|---|
| Average residence time: | 65 min |
| ICN: | 20 |

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the preparation of $C_{8-18}$ alkylpolyglycosides, comprising:

introducing alkylpolyglycosides containing alkyl groups of 1–6 carbon atoms and alcohols having 8–18 carbon atoms into a reaction column; and conducting transglycosylation of the alkylpolyglycosides in the reaction column under co- or counter-current conditions.

2. The process according to claim 1, wherein the reaction components of alkyl polyglycosides and $C_{8-18}$ alcohols are introduced into the upper portion of the column.

3. The process according to claim 1, wherein at least 10% of the alcohol having 8 to 18 C atoms is introduced into the upper portion of the reaction column and up to 90% of the alcohol is introduced into the lower portion of the column.

4. The process according to claim 3, wherein 20 to 80% of the alcohol is fed into the lower portion of the column as a vapor.

5. The process according to claim 1, wherein the alkyl polyglycoside reactant is introduced into the column together with an alcohol having 1 to 6 C atoms.

6. The process according to claim 5, wherein up to 5 parts by weight of alcohol having 1 to 6 C atoms are used per part by weight of alkyl polyglycoside.

7. The process according to claim 5, wherein said alkyl glycoside is butyl polyglucoside and said alcohol is butanol.

8. The process according to claim 1, wherein the molar ratio of alkyl polyglycoside to alcohol having 8 to 18 C atoms ranges from 1:2 to 1:15.

9. A process for the preparation of $C_{8-18}$ is alkyl polyglycosides, comprising:

introducing alkyl polyglycosides containing alkyl groups of 1 to 6 carbon atoms and alcohols having 8 to 18 carbon atoms in a reaction column having 2 to 15 plates and conducting transglycosylation of the alkyl polyglycosides in the reaction column under co- or counter-current conditions.

10. The process of claim 9, wherein said reaction column is a bubble-cap, sieve-plate, tunnel-cap or packed column.

11. The process of claim 9, wherein the average residence time for the reaction in the reaction column ranges from 5 to 15 minutes.

* * * * *

UNITED STATES PATENT AND TRADEMARK OFFICE
CERTIFICATE OF CORRECTION

PATENT NO. : 5,461,144
DATED : October 24, 1995
INVENTOR(S) : John KAHSNITZ, et al.

It is certified that error appears in the above-indentified patent and that said Letters Patent is hereby corrected as shown below:

On the title page, Item [63], the Related U.S. Application Data should read:

--Continuation of Ser. No. 863,710, Apr. 3, 1992, abandoned.--

On the title page, Item [*], the Terminal Disclaimer should read:
     --The term of this patent shall not extend beyond the expiration date of Pat. No. 5,227,480.--

Signed and Sealed this

Eleventh Day of June, 1996

Attest:

BRUCE LEHMAN

Attesting Officer     Commissioner of Patents and Trademarks